United States Patent
Baek et al.

(10) Patent No.: US 12,270,079 B2
(45) Date of Patent: Apr. 8, 2025

(54) ANALYSIS METHOD AND KIT FOR DIAGNOSIS OF UROLITHIASIS

(71) Applicant: CHA UNIVERSITY INDUSTRY-ACADEMIC COOPERATION FOUNDATION, Pocheon-si (KR)

(72) Inventors: Kwang-Hyun Baek, Seoul (KR); Jun-Hyeok Park, Seongnam-si (KR)

(73) Assignee: CHA UNIVERSITY INDUSTRY-ACADEMIC COOPERATION FOUNDATION, Pocheon-si (KR)

(*) Notice: Subject to any disclaimer, the term of this patent is extended or adjusted under 35 U.S.C. 154(b) by 872 days.

(21) Appl. No.: 17/310,163

(22) PCT Filed: Jan. 22, 2020

(86) PCT No.: PCT/KR2020/001113
§ 371 (c)(1),
(2) Date: Jul. 22, 2021

(87) PCT Pub. No.: WO2020/153759
PCT Pub. Date: Jul. 30, 2020

(65) Prior Publication Data
US 2022/0090198 A1  Mar. 24, 2022

(30) Foreign Application Priority Data
Jan. 23, 2019 (KR) .................. 10-2019-0008510

(51) Int. Cl.
*C12Q 1/686* (2018.01)
*C12Q 1/6883* (2018.01)

(52) U.S. Cl.
CPC .......... *C12Q 1/6883* (2013.01); *C12Q 1/686* (2013.01); *C12Q 2600/158* (2013.01)

(58) Field of Classification Search
CPC .............. C12Q 1/6883; C12Q 1/686; C12Q 2600/158; G01N 33/569; G01N 33/56983; G01N 2333/948; G01N 2800/345
See application file for complete search history.

(56) References Cited

U.S. PATENT DOCUMENTS 6,482,620 B1  11/2002  Glucksmann
2002/0076784 A1  6/2002  Meyers
(Continued)

FOREIGN PATENT DOCUMENTS

KR  10-2018-0050098 A   5/2018
WO  WO-2016170348 A2 * 10/2016 ............... A61P 1/00

OTHER PUBLICATIONS

Giovanelli et al., "Detection of JCPyV microRNA in blood and urine samples of multiple sclerosis patients under natalizumab therapy," J. Neurovirol, vol. 21, pp. 666-670. (Year: 2015).*
(Continued)

*Primary Examiner* — Angela M. Bertagna
*Assistant Examiner* — Francesca Filippa Giammona
(74) *Attorney, Agent, or Firm* — Vorys, Sater, Seymour and Pease LLP; Mih Suhn Koh

(57) ABSTRACT

Provided is an analytical method for providing information necessary for a diagnosis of urolithiasis, including measuring an expression level of a gene encoding a YOD1, USP6, USP19, PSMD14, or USP26 protein in a biological sample from a subject to be diagnosed; and a kit for a diagnosis of urolithiasis which is used in the analytical method.

6 Claims, 5 Drawing Sheets

Specification includes a Sequence Listing.

(56) References Cited

U.S. PATENT DOCUMENTS

| | | | |
|---|---|---|---|
| 2003/0037350 | A1 | 2/2003 | Glucksmann et al. |
| 2008/0113360 | A1* | 5/2008 | Riker .................. C12Q 1/6886 435/6.12 |
| 2010/0015645 | A1 | 1/2010 | Juo et al. |
| 2015/0158931 | A1 | 6/2015 | Ovaa et al. |
| 2016/0333341 | A1* | 11/2016 | Bhat .................... C12N 15/113 |

OTHER PUBLICATIONS

Liu et al., "ShRNA-Targeted MAP4K4 Inhibits Hepatocellular Carcinoma Growth," Human Cancer Biology, vol. 17, No. 4, pp. 710-720 (Year: 2011).*

Liu et al., Supplemental Information (Year: 2011).*

Kim et al., "Deubiquitinase YOD1 potentiates YAP/TAZ activities through enhancing ITCH stability," PNAS, vol. 114, pp. 4691-4696. (Year: 2017).*

Madan et al., "USP6 oncogene promotes Wnt signaling by deubiquitylating Frizzleds," PNAS, vol. 113, Issue 21, E2945-E2954. (Year: 2016).*

Mei et al., "The USP19 Deubiquitinase Regulates the Stability of c-IAP1 and c-IAP2," The Journal of Biological Chemistry, Colume 286, Issue 41, pp. 35380-35387. (Year: 2011).*

Mayo Clinic, "Kidney Stones," Accessed via archive.org. https://www.mayoclinic.org/diseases-conditions/kidney-stones/diagnosis-treatment/drc-20355759. (Year: 2017).*

Haq et al., "Deubiquitylation of deubiquitylases", Open Biol., 2017, vol. 7, 170016, 11 pages.

Jiang et al., "High expression of SLC26A6 in the kidney may contribute to renal calcification via an SLC26A6-dependent mechanism", PeerJ, 2018, vol. 6, e5192, 17 pages.

Li et al., "Ubiquitin-Specific Protease USP6 Regulates the Stability of the c-Jun Protein", Molecular and Cellular Biology, 2018, vol. 38, Issue 2, 11 pages.

Suen et al., "Urinary chemokines/cytokines are elevated in patients with urolithiasis", Urol Res, 2010, vol. 38, pp. 81-87.

Wang et al., "Analysis of Altered MicroRNA Expression Profiles in Proximal Renal Tubular Cells in Response to Calcium Oxalate Monohydrate Crystal Adhesion: Implications for Kidney Stone Disease", Plos One, 2014, vol. 9, Issue 7, 9 pages.

* cited by examiner

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
cgttggaatc aacagcagca ttga                                         24

<210> SEQ ID NO 2
<211> LENGTH: 23
```

```
<212> TYPE: DNA
<213> ORGANISM: Artificial Sequence
<220> FEATURE:
<223> OTHER INFORMATION: Primer

<400> SEQUENCE: 2
catccatccg ctcgttcgtg tca                                           23

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
gttctttcct tcatcgtcag ggtc                                          24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
agtgggagta gccaagagat catg                                          24

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ggtttgacac ttcaggacta ca                                            22

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
gaggtcataa gtacatccac atg                                           23

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
acttgcccat ccaatctggt ga                                            22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
```

```
acgtaactag aagcaccacg tt                                              22

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
cagccacctg tgagacctgg taa                                             23

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
ctgataactc tccgcaagta ag                                              22
```

ANALYSIS METHOD AND KIT FOR DIAGNOSIS OF UROLITHIASIS

TECHNICAL FIELD

The present invention relates to an analytical method for providing information necessary for a diagnosis of urolithiasis and a kit for a diagnosis of urolithiasis.

SEQUENCE LISTING

The Sequence Listing submitted in text format (.txt) filed on Jul. 22, 2021, named "SequenceListing.txt", created on Jul. 22, 2021 (2,132 bytes), is incorporated herein by reference.

BACKGROUND ART

The path from the formation of urine until it is excreted out of the body is called the urinary tract. Urolithiasis refers to the formation of stones in the way urine is produced, transported, and excreted. Stones may be formed anywhere in the urinary tract and vary in size and number from one to several. Urinary stones are broadly classified into kidney stones, ureter stones, and bladder stones. In actual clinical practices, bladder stones are very rare and the proportion of ureter stones is high. The number of urolithiasis patients was 280,000 in 2013, with an annual average increase rate of 2.8%. Urolithiasis occurs frequently in active 20s and 40s and occurs twice as often in men than in women. The recurrence rate thereof is more than 70%. In addition, the treatment cost is KRW 192.6 billion as of 2013, showing an average annual increase rate of 6%. The symptoms thereof include hematuria and severe pain in the flank.

Diagnosis of urolithiasis is carried out through history taking, urinalysis, blood tests, KUB (kidney ureter and bladder) radiography, jugular vein urography, and the like. In addition, since there are various cells in the urine, it is possible to perform urine cytology. Major cells in the urine include squamous epithelial cells, transitional epithelial cells, tubular epithelial cells, columnar epithelial cells, and the like, which are eliminated from the kidneys, in addition to red blood cells and white blood cells. Treatment methods are largely divided into conservative treatment and surgical treatment. Conservative treatment is a method that allows the stone to be discharged naturally without surgery; and can be used for stones less than 5 mm in diameter. For surgical treatment, extracorporeal shock wave lithotripsy and percutaneous nephrolithotomy are mainly used. These methods are complementary to each other and the treatment is determined according to the situation.

Biomarkers are a kind of markers that objectively distinguish normal or pathological conditions. Since biomarkers can predict the outcome of treatment, the role thereof in the modern medical field is very important. Among the various biomarkers observed in the human body, the biomarkers related to urolithiasis have not yet been reported.

DISCLOSURE

Technical Problem

The present inventors produced a unilateral ureteral obstruction (UUO) mouse model exhibiting urolithiasis; and identified deubiquitinating enzymes showing the difference in expressions in urolithiasis, in mRNA and protein levels, using this model. As the results thereof, it was found that specific proteins, i.e., YOD1, USP6, USP19, PSMD14, or USP26 protein, were expressed specifically high or low in the urolithiasis model. Therefore, detection of overexpression or underexpression of these proteins can be used as a biomarker for the diagnosis of urolithiasis.

Accordingly, it is an object of the present invention to provide an analytical method for providing information necessary for a diagnosis of urolithiasis, using the mRNA or protein of YOD1, USP6, USP19, PSMD14, or USP26.

In addition, it is another object of the present invention to provide a kit for a diagnosis of urolithiasis, comprising a molecule capable of measuring the expression levels of the genes encoding the YOD1, USP6, USP19, PSMD14, or USP26 protein.

Technical Solution

In accordance with an aspect of the present invention, there is provided an analytical method for providing information necessary for a diagnosis of urolithiasis, comprising measuring an expression level of a gene encoding a YOD1, USP6, USP19, PSMD14, or USP26 protein, preferably a YOD1 protein, in a subject's sample.

In the analytical method of the present invention, the subject's sample may be blood or urine. The measuring the expression level of a gene may be carried out by measuring an amount of mRNA or protein. In an embodiment, the measuring an amount of protein is carried out by Western blotting. In another embodiment, the measuring an amount of mRNA is carried out by RT-PCR or real-time PCR.

In accordance with another aspect of the present invention, there is provided a kit for a diagnosis of urolithiasis, comprising a molecule capable of measuring an expression level of a gene encoding a YOD1, USP6, USP19, PSMD14, or USP26 protein, preferably a YOD1 protein, wherein the molecule is an antibody, substrate, ligand, or cofactor, which specifically binds to the protein; or a primer having a complementary sequence specific to the gene encoding the protein.

In an embodiment, the molecule may be labeled with a detectable label. In another embodiment, the kit may be in the form of a microarray in which the primer is immobilized on a substrate.

Advantageous Effects

It has been found by the present invention that the YOD1, USP6, USP19, PSMD14, or USP26 proteins are specifically overexpressed or underexpressed in patients having urolithiasis. Therefore, the analytical method and kit according to the present invention can be usefully applied for diagnosing urolithiasis.

BEST MODE

Figure 1:
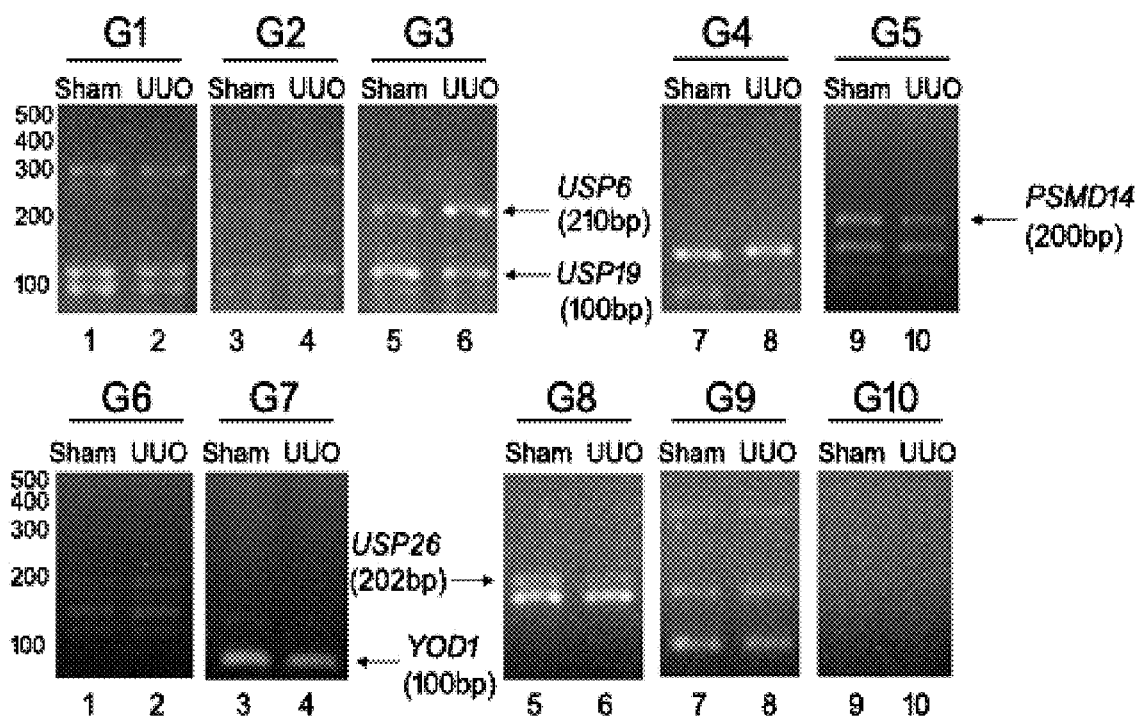
FIG. 1 shows the results obtained by performing multiplex reverse transcription polymerase chain reactions (multiplex RT-PCRs) for various deubiquitinating enzymes, exhibiting the bands of the mRNAs (i.e., the mRNAs of USP6, USP19, PSMD14, USP26, and YOD1) showing the difference in expression level in the urolithiasis model.

As used herein, the term "urolithiasis" refers to the formation of stones in the way urine is produced, transported, stored, and excreted; and includes all of the kidney stones, ureter stones, bladder stones, and urethral stones. Preferably, the urolithiasis includes kidney stones and ureter stones, and more preferably ureter stones.

The present inventors produced a unilateral ureteral obstruction (UUO) mouse model exhibiting urolithiasis; and confirmed that the kidney size was increased in the urolithiasis animal model compared to the normal group. The present inventors identified the genes encoding the deubiquitinating enzymes (i.e., the genes encoding the USP6, USP19, PSMD14, USP26, and YOD1 proteins) from the kidney tissues, which show differences in mRNA level compared to the normal group, using multiplex reverse transcription polymerase chain reaction (multiplex RT-PCR). The expression level of the mRNA of USP6 was significantly higher than that of the normal group. The expression levels of the mRNAs of USP19, PSMD14, USP26, and YOD1 were significantly lower than that of the normal group. In addition, the differences in YOD1 expression at the mRNA and protein level were confirmed in the kidney tissues of the normal group and the urolithiasis animal model, using real-time quantitative polymerase chain reaction (qRT-PCR) and Western blotting. Therefore, detection of overexpression or underexpression of these proteins can be usefully applied as a biomarker for diagnosing urolithiasis.

The present invention provides an analytical method for providing information necessary for a diagnosis of urolithiasis, comprising measuring an expression level of a gene encoding a YOD1, USP6, USP19, PSMD14, or USP26 protein, preferably a YOD1 protein, in a subject's sample.

The YOD1, USP6, USP19, PSMD14, and USP26 proteins are proteins belonging to the deubiquitinating enzyme family. For example, the NCBI accession number of the PSMD14 protein is NP_005796 and the NCBI accession number of the mRNA encoding the same is NM_005805. The NCBI accession number of the USP26 protein is Q9BXU7 and the NCBI accession numbers of the mRNA encoding the same are NM_031907.1 and NM_031388.2. There have been various isoforms of the YOD1, USP6 and USP19 proteins. The analytical method of the present invention includes measuring the expression level(s) of genes encoding the isoforms and the kit of the present invention includes a molecule(s) capable of measuring the expression level(s) of genes encoding the isoforms. The YOD1 protein is known as a protein that inhibits ubiquitination by removing ubiquitin from a protein substrate. The NCBI accession numbers of the YOD1 protein are Q5VVQ6, B2RNX3, Q5VVQ5, Q6ZRS6, Q86T63, and Q9P1L8 and the NCBI accession numbers of the mRNA encoding the same are BC137166.1 and NM_178691.4. The NCBI accession numbers of the USP6 protein are NP_001291213 and NP_004496 and the NCBI accession numbers of the mRNA encoding the same are NM_001304284, NM_004505, NM_005152, and the like. The NCBI accession numbers of the USP19 protein are NP_001186089, NP_001186090, NP_001186091, NP_006668, and NP_001338027 and the NCBI accession numbers of the mRNA encoding the same are NM_001199160, NM_001199161, NM_001199162, NM_006677, NM_001351098, and the like.

In the analytical method of the present invention, the subject's sample refers to a sample externally discharged from the human body, including e.g., blood, urine, etc. externally discharged from the human body. Blood and urine include squamous epithelial cells, transitional epithelial cells, tubular epithelial cells, columnar epithelial cells, and the like, which are eliminated from the kidneys, in addition to red blood cells and white blood cells. It is possible to measure expression level of the gene(s) from the blood (preferably, the blood externally discharged from a dialysis patient, etc.) and urine.

The analytical method of the present invention includes measuring an expression level of a gene encoding the YOD1, USP6, USP19, PSMD14, or USP26 protein. The genetic sequence encoding each of the above proteins may be a gene known in GenBank as described above.

The measuring the expression level of a gene may be carried out by measuring an amount of mRNA or protein according to a method conventionally used in the field of biotechnology. In an embodiment, the measuring an amount of protein(s) is carried out by Western blotting. In said analytical method according to Western blotting, when the expression level of the USP6 protein is significantly higher than that of a normal group and/or the expression level of the USP19, PSMD14, USP26, or YOD1 protein is significantly lower than that of a normal group, the subject may be considered as a urolithiasis patient. In addition, the measuring an amount of mRNAs encoding the proteins is carried out by reverse transcription PCR (RT-PCR), real-time PCR, and the like.

The present invention also provides a kit for a diagnosis of urolithiasis, comprising a molecule capable of measuring an expression level of a gene encoding a YOD1, USP6, USP19, PSMD14, or USP26 protein, preferably a YOD1 protein, wherein the molecule is an antibody, substrate, ligand, or cofactor, which specifically binds to the protein; or a primer having a complementary sequence specific to the gene encoding the protein.

The protein(s) may be used to prepare a polyclonal antibody or a monoclonal antibody and a diagnostic kit comprising the antibody may be also prepared, according to a method conventionally used in the field of biotechnology. And, since the function of the protein(s) has been revealed, the kit of the present invention may be prepared to comprise a substrate, a ligand, or a cofactor thereto. In addition, a primer having a complementary sequence specific to the gene encoding the protein(s) may be prepared and a diagnostic kit comprising the primer may be also prepared, according to a method conventionally used in the field of biotechnology.

In the diagnostic kit of the present invention, a molecule capable of measuring an expression level of a gene encoding the protein(s) may be labeled with a detectable label (e.g., a chromophore, etc.). And, the diagnostic kit of the present invention may be in the form of a microarray, e.g., in the form of a chip such as a DNA chip or a protein chip, in which the primer is immobilized on a substrate.

Hereinafter, the present invention will be described more specifically by the following examples. However, the following examples are provided only for illustrations and thus the present invention is not limited to or by them.

EXAMPLES

1. Test Methods (1) Preparation of Samples

An animal model of urolithiasis was produced by tying the ureter of a mouse and raising it for 6 weeks. Kidney tissues were excised from normal mice and the urolithiasis animal model.

(2) RNA Extraction and cDNA Synthesis

The respective RNA was extracted from the excised kidney tissues using a Trizol solution. cDNAs were synthesized from the respective RNA having the same concentration and then diluted for performing multiplex reverse transcription polymerase chain reactions (multiplex RT-PCRs). GAPDH was used as a housekeeping gene. The respective cDNA diluted to the same concentration was subject to multiplex reverse transcription polymerase chain reactions (multiplex RT-PCRs) using the 2× premix (Solgent) for multiplex RT-PCR and the primers (see Table 1). The PCR (a total of 40 cycles) was performed under the conditions of: 20 seconds at 95° C. for denaturation, 40 seconds at 60° C. for annealing, and 60 seconds at 72° C. for extension.

TABLE 1

| Gene | SEQ ID NO | Primer | Sequence |
|---|---|---|---|
| USP6 | 1 | Forward primer | CGTTGGAATCAACAGCAGCATTGA |
|  | 2 | Reverse primer | CATCCATCCGCTCGTTCGTGTCA |
| USP19 | 3 | Forward primer | GTTCTTTCCTTCATCGTCAGGGTC |
|  | 4 | Reverse primer | AGTGGGAGTAGCCAAGAGATCATG |
| PSMD14 | 5 | Forward primer | GGTTTGACACTTCAGGACTACA |
|  | 6 | Reverse primer | GAGGTCATAAGTACATCCACATG |
| YOD1 | 7 | Forward primer | ACTTGCCCATCCAATCTGGTGA |
|  | 8 | Reverse primer | ACGTAACTAGAAGCACCACGTT |
| USP26 | 9 | Forward primer | CAGCCACCTGTGAGACCTGGTAA |
|  | 10 | Reverse primer | CTGATAACTCTCCGCAAGTAAG |

(3) Extraction of Proteins and Measurement of the Levels Thereof

The excised kidney tissues were ground using liquid nitrogen and a mortar. Proteins were extracted with a lysis buffer and then subject to Western blotting for confirming the levels thereof.

(4) Evaluation and Analysis of the Results

The products of the multiplex reverse transcription polymerase chain reactions (multiplex RT-PCRs) were electrophoresed on a 2% agarose gel. The respective bands amplified from the cDNAs by the primers thereof were identified through ChemiDoc gel Imaging System (Bio-Rad). In addition, the proteins were detected with the respective membrane subjected to Western blotting.

2. Results and Discussion

Figure 2:
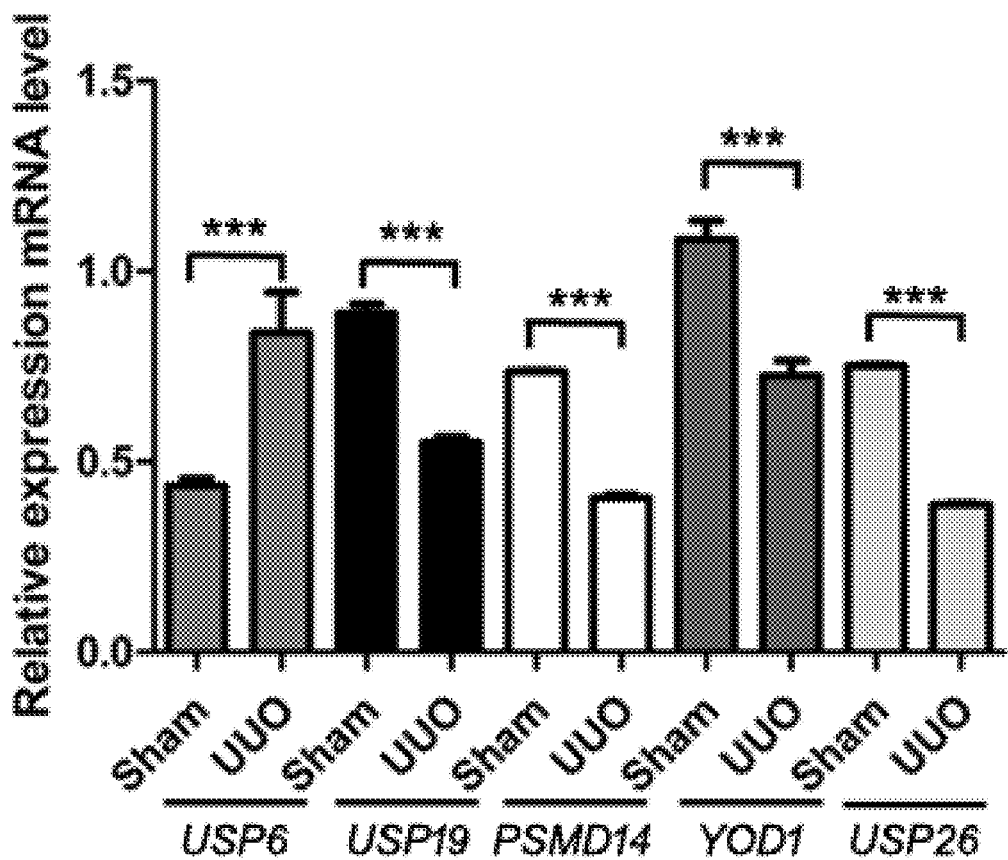
FIG. 2 shows the quantitative analysis results of the relative mRNA expression levels of the bands of FIG. 1 using the Image J program.
Figure 3:
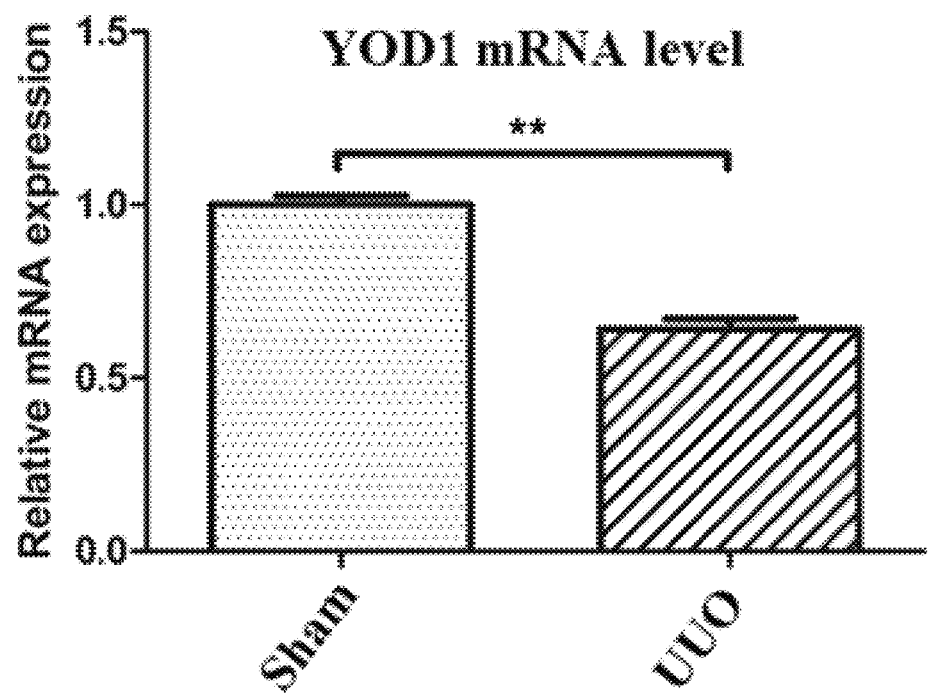
FIG. 3 shows the results obtained by measuring the amount of expression in the mRNA level of the YOD1 protein using quantitative real-time polymerase chain reaction (qRT-PCR).
Figure 4:
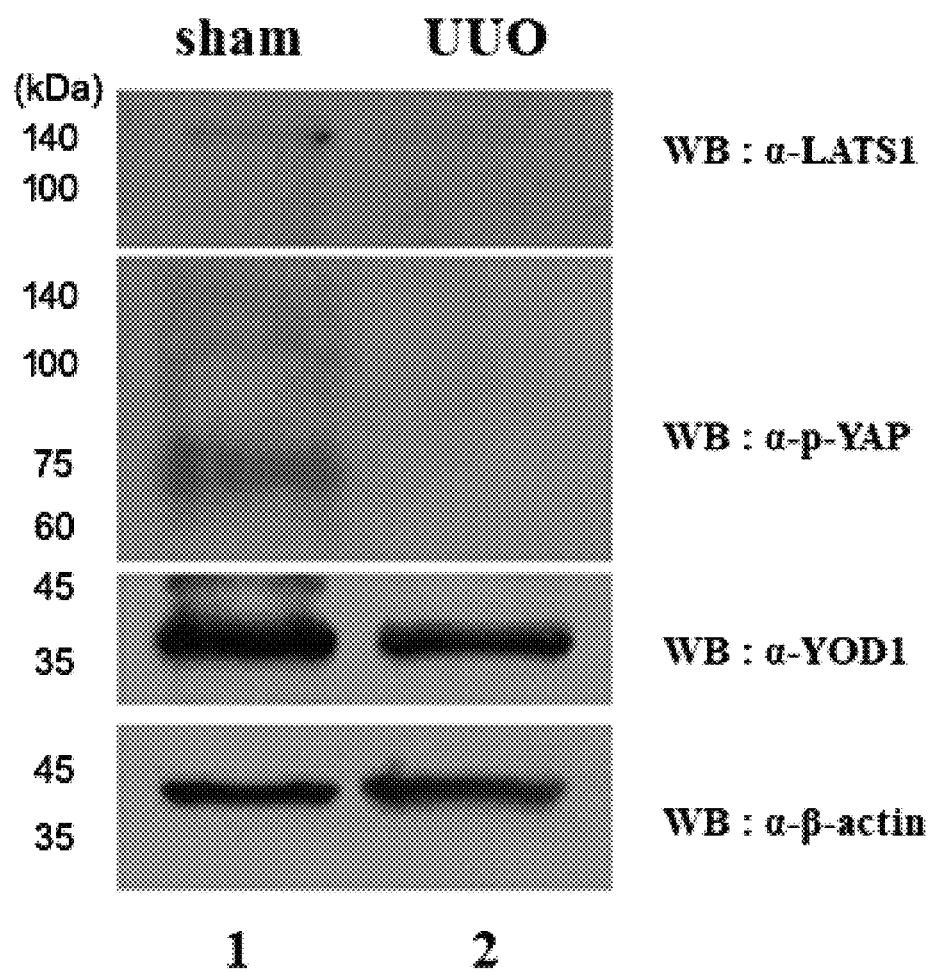
FIG. 4 shows the results obtained by confirming the expression levels of the YOD1 protein and the proteins related to the Hippo signaling pathway, using Western blotting.
Figure 5:
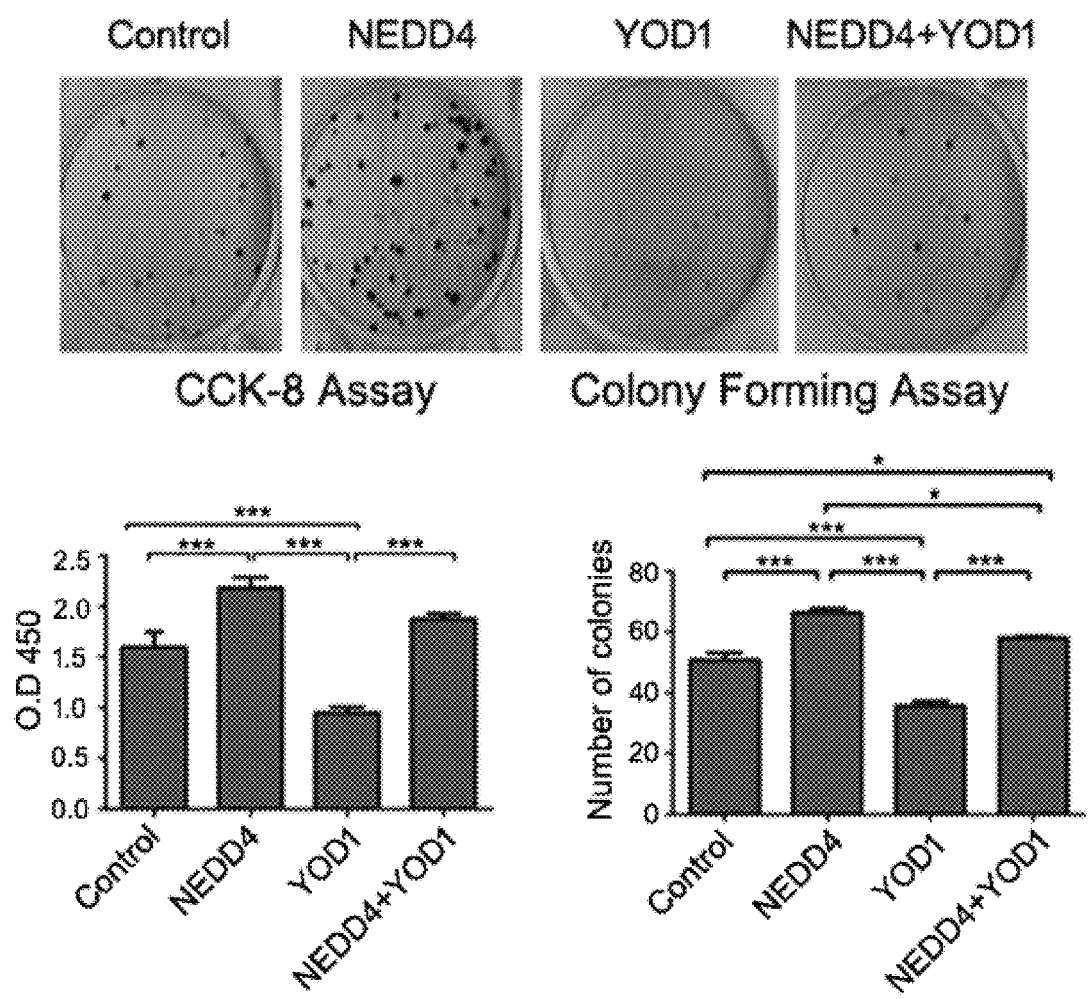
FIG. 5 shows the results obtained by confirming the reduction in proliferation of human kidney cells when YOD1 was overexpressed in human kidney cells.

After kidney tissues were excised from the urolithiasis animal model, the RNAs were extracted and cDNAs were synthesized. After performing multiplex reverse transcription polymerase chain reactions (multiplex RT-PCRs) by mixing the primers and cDNAs divided into 10 groups, the expression levels were confirmed by agarose gel electrophoresis to identify the proteins (i.e., USP6, USP19, PSMD14, USP26, and YOD1 proteins) that showed the difference in expression level in the urolithiasis model compared to the normal group (FIG. 1). The quantitative analysis results of the relative mRNA expression levels of the identified protein bands using the Image J program are shown in FIG. 2. From the results of FIG. 2, the USP6 protein showed significantly higher expression in the urolithiasis animal model compared to the normal group, and the USP19, PSMD14, USP26, and YOD1 proteins showed significantly lower expression in the urolithiasis animal model compared to the normal group. The decrease in mRNA level of the YOD1 protein was verified using quantitative real-time polymerase chain reaction (qRT-PCR) (FIG. 3), and the decrease in expression level of the YOD1 protein was also verified using Western blotting (FIG. 4). In addition, as a result of overexpressing YOD1 in human kidney cells, it was confirmed that the proliferation of human kidney cells was reduced (FIG. 5). Therefore, it can be confirmed that if YOD1 is reduced in the same way in mice and humans, the proliferation of the kidneys can be increased.

As can be seen from the above results, urolithiasis can be diagnosed by measuring the expression level of the YOD1, USP6, USP19, PSMD14, or USP26 protein and therefore the proteins or genes encoding these proteins can be used as a biomarker for diagnosing urolithiasis.

The invention claimed is:

1. A method for diagnosis and treatment of urolithiasis, comprising
   (a) measuring an expression level of a gene encoding a YOD1, USP6, USP19, PSMD14, or USP26 protein in a biological sample from a subject to be diagnosed,
   (b) comparing the expression level obtained in step (a) and a corresponding expression level in a person without urolithiasis,
   (c) diagnosing the subject with urolithiasis based on a finding that either the expression level of the gene encoding the USP6 protein was significantly higher than that of a person without urolithiasis or the expression level of the gene encoding the USP19, PSMD14, USP26, or YOD1 protein was significantly lower than that of a person without urolithiasis, and
   (d) providing the urolithiasis patient with a surgical treatment of extracorporeal shock wave lithotripsy or percutaneous nephrolithotomy, or a non-surgical treatment allowing a kidney stone to be discharged naturally without surgery.

2. The method according to claim 1, wherein step (a) comprises measuring an expression level of the gene encoding the YOD1 protein.

3. The method according to claim 1, wherein the biological sample is a blood sample or a urine sample.

4. The method according to claim 1, wherein the measuring of the expression level of the gene is carried out by measuring an amount of mRNA or protein.

5. The method according to claim 4, wherein the measuring an amount of protein is carried out by Western blotting.

6. The method according to claim 4, wherein the measuring an amount of mRNA is carried out by RT-PCR or real-time PCR.

* * * * *